United States Patent
Chen et al.

(10) Patent No.: US 10,088,471 B1
(45) Date of Patent: Oct. 2, 2018

(54) IMMUNOGLOBULIN G MRNA BASED PLASMA CELL SEPARATION AND ANTIBODY GENE CLONING

(71) Applicants: KunHua Chen, San Diego, CA (US); Xiangqian Ma, San Diego, CA (US)

(72) Inventors: KunHua Chen, San Diego, CA (US); Xiangqian Ma, San Diego, CA (US)

(73) Assignee: ExonBio, LLC, San Diego, CA (US)

( * ) Notice: Subject to any disclaimer, the term of this patent is extended or adjusted under 35 U.S.C. 154(b) by 0 days.

(21) Appl. No.: 15/467,233

(22) Filed: Mar. 23, 2017

Related U.S. Application Data

(60) Provisional application No. 62/321,202, filed on Apr. 12, 2016.

(51) Int. Cl.
| | |
|---|---|
| *C12N 15/10* | (2006.01) |
| *G01N 33/50* | (2006.01) |
| *C12Q 1/6879* | (2018.01) |
| *C12N 15/85* | (2006.01) |

(52) U.S. Cl.
CPC ......... *G01N 33/5005* (2013.01); *C12N 15/85* (2013.01); *C12Q 1/6879* (2013.01); *C12Q 2600/156* (2013.01); *C12Q 2600/158* (2013.01)

(58) Field of Classification Search
None
See application file for complete search history.

(56) References Cited

PUBLICATIONS

Tiller et al, J. Immunological Methods 329: 112 (2008).*

* cited by examiner

*Primary Examiner* — James Martinell
(74) *Attorney, Agent, or Firm* — Lili Chen

(57) ABSTRACT

Disclosed are IgG mRNA based methods for cloning antigen specific antibody gene from single plasma cells. The present invention provides a intracellular IgG mRNA based method for identifying individual plasma cells and amplifying antibody genes with cognate pairing of the heavy and light chain from the identified single plasma cells.

18 Claims, 4 Drawing Sheets

Specification includes a Sequence Listing.

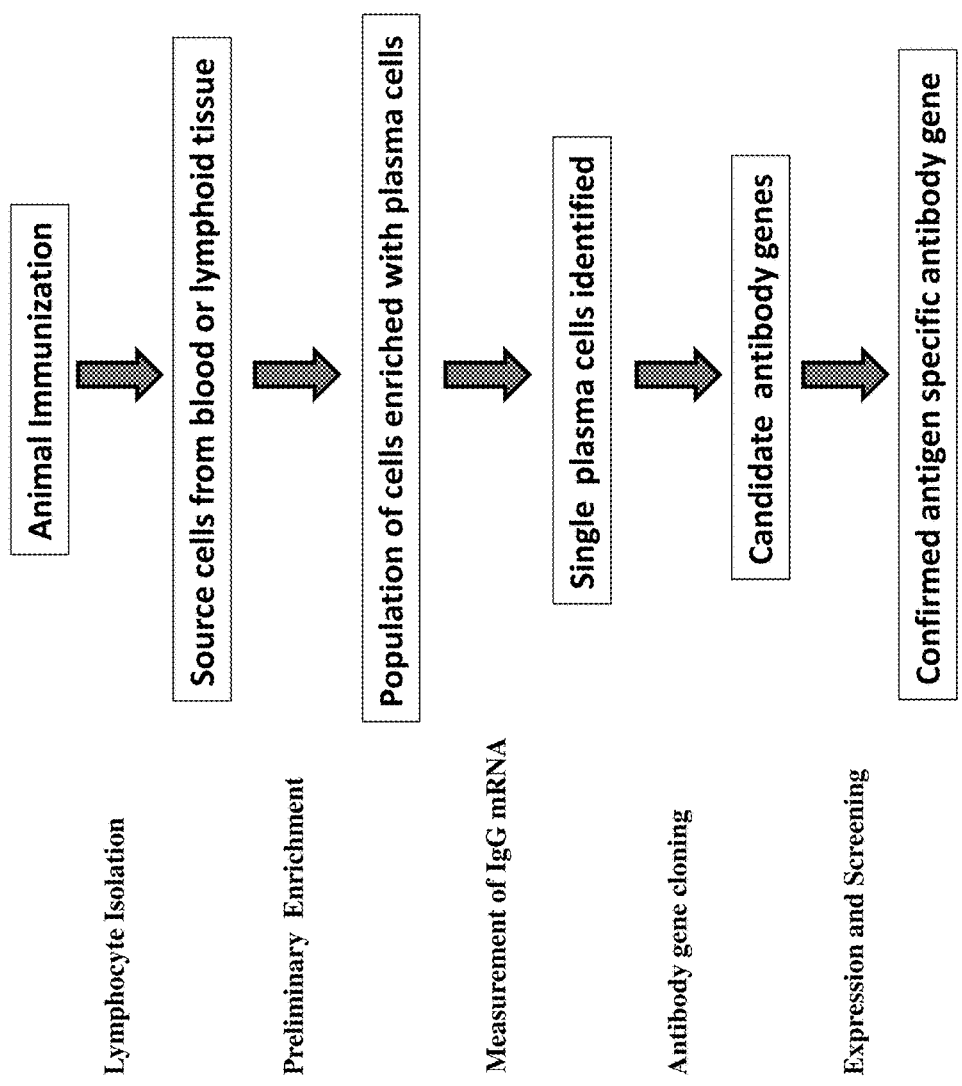

SEQUENCE LISTING

<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: DNA Primer

<400> SEQUENCE: 1

```
caccaaagtg gacaagac                                               18

<210> SEQ ID NO 2
<211> LENGTH: 18
<212> TYPE: DNA
<213> ORGANISM: Artificial Sequence
<220> FEATURE:
<223> OTHER INFORMATION: DNA Primer

<400> SEQUENCE: 2
ggaagatgaa gacagacg                                               18

<210> SEQ ID NO 3
<211> LENGTH: 20
<212> TYPE: DNA
<213> ORGANISM: Artificial Sequence
<220> FEATURE:
<223> OTHER INFORMATION: DNA Primer

<400> SEQUENCE: 3
ttgcaccctc gacatgcagc                                             20

<210> SEQ ID NO 4
<211> LENGTH: 19
<212> TYPE: DNA
<213> ORGANISM: Artificial Sequence
<220> FEATURE:
<223> OTHER INFORMATION: DNA Primer

<400> SEQUENCE: 4
gcttctcctg gtcgctgtg                                              19

<210> SEQ ID NO 5
<211> LENGTH: 21
<212> TYPE: DNA
<213> ORGANISM: Artificial Sequence
<220> FEATURE:
<223> OTHER INFORMATION: DNA Primer

<400> SEQUENCE: 5
tcttgtccac tttggtgttg g                                           21

<210> SEQ ID NO 6
<211> LENGTH: 18
<212> TYPE: DNA
<213> ORGANISM: Artificial Sequence
<220> FEATURE:
<223> OTHER INFORMATION: DNA Primer

<400> SEQUENCE: 6
gggctcctgc tgctctgg                                               18

<210> SEQ ID NO 7
<211> LENGTH: 20
<212> TYPE: DNA
<213> ORGANISM: Artificial Sequence
<220> FEATURE:
<223> OTHER INFORMATION: DNA Primer

<400> SEQUENCE: 7
atggtgggaa gakgaggaca                                             20

<210> SEQ ID NO 8
<211> LENGTH: 21
<212> TYPE: DNA
```

```
<213> ORGANISM: Artificial Sequence
<220> FEATURE:
<223> OTHER INFORMATION: DNA Primer

<400> SEQUENCE: 8
cttctcctgg tcgctgtgct c                                      21

<210> SEQ ID NO 9
<211> LENGTH: 19
<212> TYPE: DNA
<213> ORGANISM: Artificial Sequence
<220> FEATURE:
<223> OTHER INFORMATION: DNA Primer

<400> SEQUENCE: 9
accgtggagc tgggtgtgt                                         19

<210> SEQ ID NO 10
<211> LENGTH: 18
<212> TYPE: DNA
<213> ORGANISM: Artificial Sequence
<220> FEATURE:
<223> OTHER INFORMATION: DNA Primer

<400> SEQUENCE: 10
tgctctggct cccaggtg                                          18

<210> SEQ ID NO 11
<211> LENGTH: 25
<212> TYPE: DNA
<213> ORGANISM: Artificial Sequence
<220> FEATURE:
<223> OTHER INFORMATION: DNA Primer

<400> SEQUENCE: 11
atggtgggaa gakgaggaca gtagg                                  25
```

IMMUNOGLOBULIN G MRNA BASED PLASMA CELL SEPARATION AND ANTIBODY GENE CLONING

CROSS-REFERENCES AND RELATED APPLICATIONS

This application claims priority to U.S. Provisional Application No. 62/321,202, entitled "Immunoglobulin G mRNA based plasma cell separation and antibody gene cloning", filed Apr. 12, 2016, the content of which is herein incorporated by reference in its entirety.

BACKGROUND OF THE INVENTION

Field of the Invention

The present invention is in the field of molecular biotechnologies. In particular, it relates to methods of selecting single plasma cells and cloning antibody genes from the single plasma cells.

Description of the Related Art

It has been long recognized that the rabbit immune system has the potential to generate highly specific antibodies with high affinity. Currently, there are several methods available for rabbit antibody generation. Traditionally, Epitomics, now part of Abcam had the license for rabbit hybridoma technology. Similar to mouse hybridoma technology, isolated splenocytes are fused with rabbit myeloma cells and cloned by a limited dilution. Hybridoma technology is robust and reliable, but this technology has several inherent disadvantages. Firstly, all B cells among the isolated splenocytes have the same opportunity to fuse with Myeloma cells. A majority of these B cells are naïve or at the early stage of maturation. Therefore, a large number of hybridoma cell lines have to be screened for antibody selection. For selecting a diagnostic antibody, usually 40 96-well plates are needed to be cultured and screened, requiring a large amount of labor and materials. Secondly, to obtain a monoclonal hybridoma cell line, two rounds of limited dilution cloning are required, which may take 3-4 months. Thirdly, a rabbit hybridoma is not as stable as a mouse hybridoma, and some of the hybridoma lines have been found to slow down or stop cell division during the culture. That could cause the loss of interesting clones.

B cell immortalization is another technology developed for rabbit antibody generation. It is very similar to hybridoma technology, but instead of myeloma cell fusion, it uses Epstein-Barr virus to immortalize B cells. The immortalized B cells can be continuously cultured and secrete antibodies. Similar to hybridoma, the efficiency of virus induced immortalization is low and some of the immortalized clones are not stable. Therefore, they are time-consuming and complicated. To avoid the technical limitations, several newer methods had been used in rabbit antibody development.

Phage display and yeast display technologies have been used for a long time. With naïve libraries or synthesized libraries, phage- or yeast-display have the benefit of allowing the selection of antibodies without immunization of animals. However, antibodies selected from a naïve library or synthetic library have usually been found to have low affinity, as antibody affinity maturation is an important step for finding high affinity antibodies that can be used in a diagnostic immunoassay. Therefore, the high cost of screening and lack of antibody diversity and affinity prevent these methods from being applied to diagnostic antibody development. For an immunized library, the mix of heavy chain (HC) and light chain (LC) genes make the library size exponentially higher. Since rabbit antibodies are encoded by two separate heavy chain and light chain genes, making a single display library will mix the HC and LC from different cells and lose the original HC and LC pairing. The random pairing of HC and LC in the library will result in most of the nonnative pairs with low or no affinity, and finding the native pairing would require very large libraries and extensive screening for a surface-displayed antibody. The selected clones may not always represent the optimum available due to the factors such as phage or yeast growth rate, non-specific binding, and other selection pressures that can introduce bias in the selection process.

Single-cell culture based methods have experienced a breakthrough recently. Single B cells have been isolated and deposited into 96-well plates and cultured under stimulation of feeder cells and signaling molecules (Seeber S, et al. PLoS One. 9(2):e86184, 2014). After incubation periods of about 10 days, enough IgG is secreted into the supernatant to allow for screening. This straight forward technology avoids the bias of library screening, but not all B cells can equally well survive and grow in a single-cell format. Some of the cell types, such as terminally differentiated plasma cells, are more difficult to culture than the others. Thus, single cell culture based screening may have severe growth bias. With only ~10% of the wells contains antibody producing cells, the number of single cell cultures need to be reasonably large, therefore, high throughput automation may be necessary, thus limiting the application of this technology in therapeutic antibody development.

In the process of searching for an HIV neutralization antibody, single memory cell isolation and its antibody gene amplification have been developed in recent years (Scheid J F, et al. Nature. 458(7238):636-40, 2009). The advantage of this method is that memory cells usually contain high affinity mature antibodies, so that direct screening of memory cells is much more efficient than screening of total B cells. In human and mouse samples, memory cell surface markers had been developed, confirmed and used in conjunction with flow cytometry to isolate and deposit memory cells to 96-well plates. This method had been proved to be feasible and highly efficient. However, all these methods depend on the development of characteristic surface markers for selection of cells of interest. For cells that lack characteristic surface markers, these methods are not applicable. For example, in rabbit samples, no equivalent cell surface markers for memory B cells have been found, therefore isolation of rabbit memory cells is not currently feasible. The surface marker based methods can be also biased by the expression level of the specific surface marker that cells expressing low levels of the surface marker may be under the selection radar. Plasma cells are a group of cells at the end stage of B cell development that express large amounts of high affinity mature antibodies, which are good candidates to be used for high affinity antibody screening. Plasma cells have lost specific surface markers during development, making it difficult to use the above surface marker based selection methods. There is a need to develop general selection methods for plasma cells that uses selection criteria other than surface markers.

The lack of specific surface markers for plasma cells prompted us to search for a method of using internal mRNA marker. Plasma cells are the major cell type that contribute to antibody generation in peripheral blood. A general characteristic of all plasma cells is the high expression of IgG genes and high secretion of IgG. These cells have up to 1000-fold more IgG mRNA than those of other B cells. Based on this basic characteristics, we have designed a two-step screening approach to isolate plasma cells for single cell antibody gene amplification and cloning, which allows isolation of plasma cells from species like rabbit, chicken, llama that lack specific surface markers for plasma cells.

SUMMARY OF THE INVENTION

The object of this invention is to identify single plasma cells for cloning high affinity antigen specific antibody genes. Plasma cells are terminally differentiated B cells that are specialized at expressing large amounts of high affinity mature antibodies, making them good candidates for high affinity monoclonal antibody screening. Plasma cells represents a very small portion of lymphoid cells (<1%) and have lost specific surface markers during development, which makes it difficult to use the conventional surface marker based selection methods. Based on a unique feature of plasma cells that they express much more IgG than other B cell types, the present invention provides a robust two-step screening method for identifying single plasma cells and cloning antibody genes from the single plasma cells thus identified. The present invention first enriches plasma cells from peripheral blood cells or lymphoid cells of an immunized animal using conventional surface marker based methods. Secondly, the enriched cells are dispersed into single cells in individual containers, where mRNA of individual cells are extracted and converted to cDNA, and levels of IgG mRNA are quantitatively determined for individual cells. The single cells with higher level of IgG mRNA are identified as plasma cells. Thirdly, once single plasma cells are identified, their cDNA are used for cloning of antibody genes into a mammalian expression vector. The antibody genes with native heavy and light chain pairs can then be introduced into a mammalian cells to express antibody proteins that can be screened for high affinity antibodies specific for target antigen. The present invention is the first one to use cytoplasmic mRNA as a marker for plasma cell identification for the purpose of antibody development. This method allows identification of individual plasma cells and cloning of high affinity antibody genes from such identified plasma cells. It greatly increases the efficiency of finding genes encoding high affinity antibodies and significantly decreases the workload of downstream screening.

In one embodiment, the present invention provides a method for cloning antigen specific antibody genes from single plasma cells, comprising the steps of: a) collecting a population of cells enriched with plasma cells expressing antibodies specific for the antigen; b) dispersing the population of cells enriched with plasma cells as single cells into individual containers; c) measuring the amount of IgG mRNA in each of the single cells and dividing the single cells into groups with high and low levels of IgG mRNA, wherein single cells with high levels of IgG mRNA are identified as plasma cells; and d) cloning antigen-specific antibody genes from the identified single plasma cells.

In one embodiment, variable regions of HC and LC are amplified from cDNA of single plasma cells and linked with respective constant regions of HC and LC to make functional antibodies that can bind to antigens such as Fab (antigen binding fragment) and full-length antibody genes. The variable region of HC and LC can also be linked by a short linker peptide to form a single chain variable fragment (scFv), which also has antigen binding activity. The linker peptide usually has 10 to 25 amino acids and connects the C-terminus of the HC variable region to the N-terminus of the LC variable region, or vice versa.

In one embodiment, the present invention further comprises a means of expressing the antigen-specific antibody genes (e.g. in a cell line) and screening for antibody genes expressing high affinity antibody against the antigen.

In one embodiment of the present invention, the population of cells enriched with plasma cells are collected from source cells of blood, lymph, bone marrow, spleen, tonsil, lymph nodes, or other lymphoid tissues from an animal immunized with the antigen. They can also be collected from blood cells, lymphocytes or bone marrow derived cells that are sensitized by the antigen in vitro to become antibody producing cells like plasma cells.

In one embodiment of the present invention, the methods for enriching plasma cells from the source cells include using surface marker based selection methods. The surface markers used for selection may be preferably expressed on plasma cells. They may also be expressed on cells other than plasma cells (e.g. other type of B cells). These methods include, but not limited to, selecting cells that bind to the antigen, anti-plasma cell antibodies, antibodies for plasma cell-specific markers, antibodies for B-cell specific markers, or anti-IgG antibody. Since plasma cells are known to have more abundant endoplasmic reticulum (ER) than other cells, using ER-specific dyes to select ER rich cells can also enrich plasma cells.

In one embodiment of the present invention, levels of IgG mRNA of individual cells of the enriched cell population are measured using methods appropriate for determination of mRNA level at single cell level including, but not limited to, quantitative PCR (polymerase chain reaction), single cell RNA detection technologies (e.g. SmartFlare™ technology, EMD Millipore) or other hybridization methods. Plasma cells are reported to generate significantly more IgG mRNA than other B cells. In some embodiment, the single cells are divided into groups based on IgG mRNA levels, the group of cells with significantly higher IgG mRNA are identified as plasma cells. In some embodiment, plasma cells are identified as cells expressing high levels of IgG mRNA which have at least 8 fold, 8 to 100 fold, 100 to 1000 fold or 1000-10,000 fold more IgG mRNA than those B cells expressing low levels of IgG mRNA.

In one embodiment of the present invention, the quantitative measurement of the IgG expression level is performed simultaneously with PCR amplification to clone antibody genes, wherein a fluorescent dye is added in the PCR system to monitor the formation of PCR products. The fluorescent dye can be sequence specific dye that specifically recognizes the formation of IgG DNAs, or it can be a nonspecific dye that can bind to and measure the formation of all the double-stranded DNA.

In one embodiment of the present invention, variable regions of antibody genes are amplified from cDNAs of single plasma cells and are assembled with the constant region to make functional antibody genes.

In one embodiment of the present invention, the cloned antigen-specific antibody genes are transferred into cells to express antigen-specific antibodies, and the expressed antibodies are screened for their ability to bind to the antigen.

In a preferred embodiment, the present invention provides a method of cloning antigen-specific antibody genes from single plasma cells comprises the steps of: a) collecting source cells from blood, lymph, spleen, lymph nodes, tonsil, bone marrow and/or other lymphoid tissues of an animal immunized with the antigen, or from blood cells, lymphocytes or bone marrow derived cells that are sensitized to the antigen in vitro; b) obtaining a population of cells enriched with plasma cells by selecting cells from the source cells that bind to the antigen and anti-IgG antibody; c) dispersing the population of cells enriched with plasma cells as single cells into individual containers; d) measuring and comparing IgG mRNA levels in each of the dispersed single cells, wherein single cells with high IgG mRNA levels are identified as plasma cells; e) cloning the antigen-specific antibody genes from the above identified single plasma cells; and f) transferring the antigen-specific antibody genes into host cells and screening for expressed antibody genes that can specifically bind to the antigen. In some embodiment, the IgG mRNA level in the single cells are measured using quantitative PCR.

In some embodiment, the source cells can be collected from a immunized nonhuman animal or a human vaccinated with the antigen. The source cells can also be blood cells, lymphocytes, or cells derived from bone marrow that are sensitized by the antigen in vitro to become antibody producing cells.

In some embodiment, the plasma cells are enriched by selecting cells from the source cells that bind to fluorescently labeled antigen and anti-IgG antibody using a fluorescence-activated cell sorting (FACS) method. In some embodiment, cells expressing IgM antibodies can be excluded by selecting IgM negative cell population using methods such as FACS. In some embodiment, plasma cells can be further enriched by selecting cells with medium to large size among source lymphocytes using appropriate light scattering selection parameters in FACS.

In some embodiment, the antigen-specific antibody genes are transferred into a mammalian cells (e.g. HEK293 cells, CHO cells and Hela cells) to express the antigen-specific antibodies, whose ability to bind the antigen can be assessed by conventional immunoassays.

In another embodiment, the present invention provides a method for identifying single plasma cells, comprising the steps of: a) collecting a population of cells enriched with plasma cells; b) disseminating the population of cells enriched with plasma cells into single cells; and c) measuring the amount of IgG mRNA in each of the single cells and dividing the single cells into groups with high and low levels of IgG expression, wherein single cells with high levels of IgG expression are identified as plasma cells.

BRIEF DESCRIPTION OF THE DRAWINGS

FIG. 1. Flow chart of the procedure for cloning antibody gene from single plasma cells.

Figure 2A:
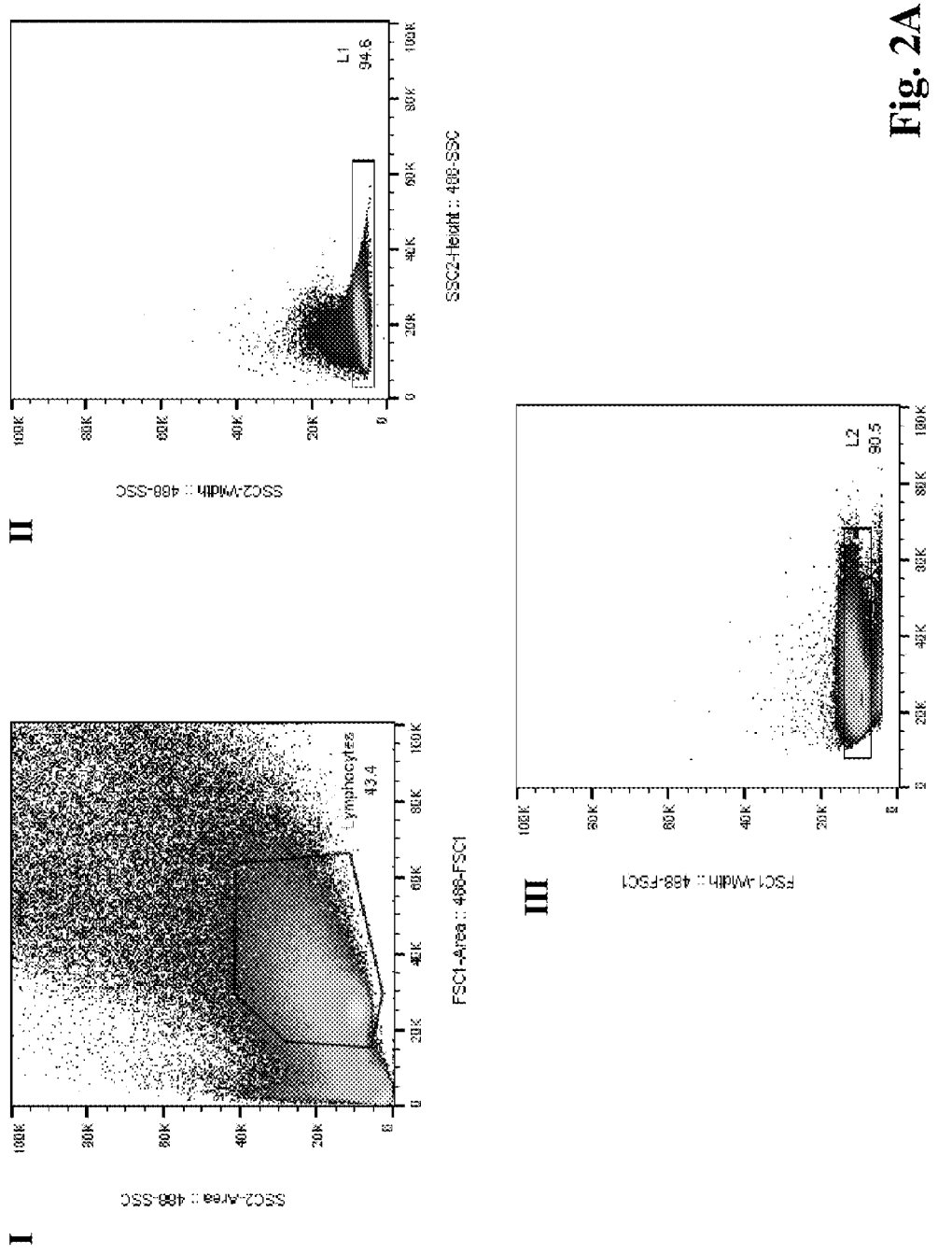
FIGS. 2A-2B. FACS sorting of rabbit bone marrow cells to enrich plasma cells. Bone marrow cells are labeled with Dylight 650 conjugated anti-rabbit IgG and Dylight 488 conjugated antigen, LP-PLA2. Cells are gated and selected using gating parameters as shown in FIG. 2A I, II, III, FIG. 2B IV, and V. Singlet lymphocytes were selected based on gating criteria set in FIG. 2A I, II and III. Cells with moderate labeling of IgG antibody and high labeling of LP-PLA2 were selected based on gating criteria set in FIG. 2B IV and V, which are enriched with plasma cells and sorted into wells of a microplate with one cell per well.
Figure 2B:
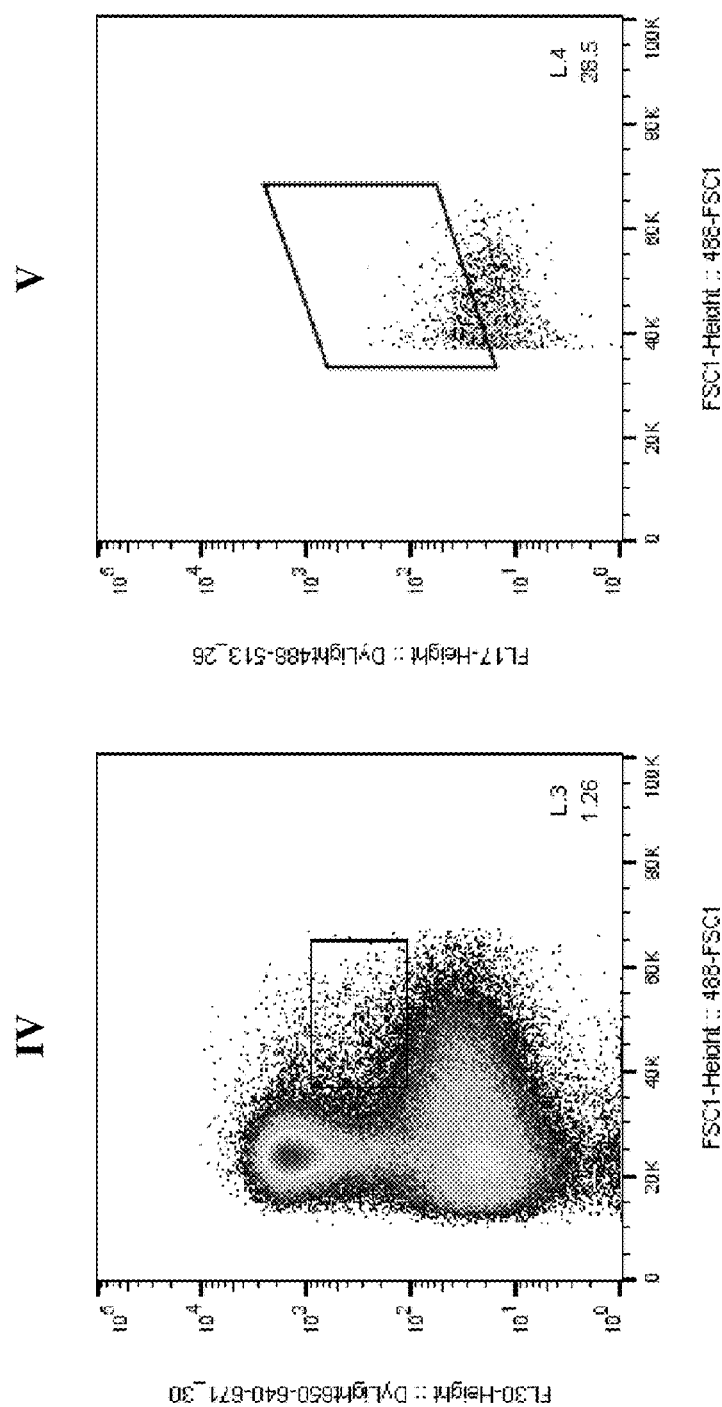
Figure 3:
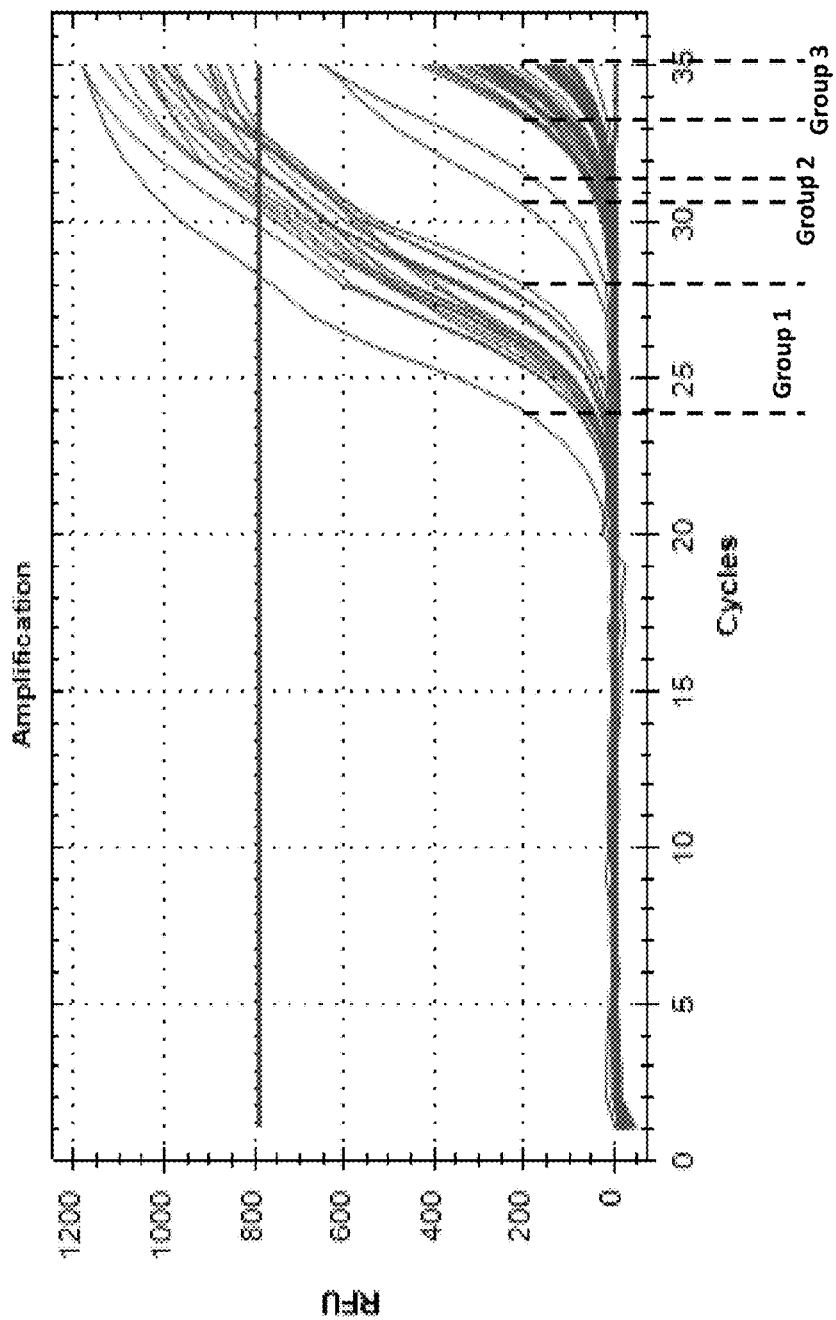
FIG. 3. qPCR of individual cells enriched by FACS to identify plasma cells. Quantitative PCR was performed in FACS sorted cells simultaneously with the PCR amplification to clone variable regions of IgG antibody genes. A fluorescent dye, SYBR® Green, was added to the PCR amplification to monitor the formation of PCR product in real time. The FACS sorted cells are divided into three groups based on their expression levels of IgG: high (group 1), low (group 2), and very low/no expression (group 3). The group with high levels of IgG expression (group 1) is identified as plasma cells, which usually expresses 8 to 1000 more IgG than that of the group with low levels of IgG (group 2).

Table 1. ELISA screening of recombinant antibodies after transfecting HEK293 cells with the cloned antibody genes. Supernatants from HEK293 cells transfected with cloned antibody genes were incubated with Lp-PLA2 coated plate, and the bound Lp-PLA2 antibody was detected by a HRP conjugated anti-rabbit antibody and measured by the absorbance at wavelength 450 nm. Out of the 14 cells tested for antibody expression, 4 cells showed positive Lp-PLA2 binding activities.

TABLE 1

Indirect ELISA screening for Lp-PLA2 positive clones.

| | Clone # | | | | | | |
|---|---|---|---|---|---|---|---|
| | 1 | 2 | 3 | 4 | 5 | 6 | 7 |
| Duplicate #1 | 0.049 | 0.079 | 1.951 | 0.119 | 0.076 | 0.068 | 0.536 |
| Duplicate #2 | 0.127 | 0.056 | 1.844 | 0.098 | 0.089 | 0.105 | 0.246 |

| | Clone # | | | | | | |
|---|---|---|---|---|---|---|---|
| | 8 | 9 | 10 | 11 | 12 | 13 | 14 |
| Duplicate #1 | 0.065 | 1.870 | 0.054 | 0.910 | 0.082 | 0.054 | 0.046 |
| Duplicate #2 | 0.048 | 1.897 | 0.077 | 1.460 | 0.079 | 0.088 | 0.046 |

DETAILED DESCRIPTION

All referenced publications are incorporated herein by reference to disclose and describe the methods and/or materials in connection with which the publications are cited. It is understood that the present disclosure supersedes any disclosure of an incorporated publication to the extent there is a contradiction.

Unless defined otherwise, all technical and scientific terms used herein have the same meaning as commonly understood by one of ordinary skill in the art to which this invention belongs. The following terms are defined below for the sake of clarity and ease of reference.

All references to the plural herein shall also mean the singular and to the singular shall also mean the plural unless the context otherwise requires.

The term "lymphocyte" as used herein refers to a subtype of white blood cells with a single round nucleus that mediate the production of immunity, occurring especially in lymphatic system. Lymphocytes are the main cell types in lymph, which include B cells, T cells and natural killer cells.

The term "plasma cell" as used herein refers to a terminally differentiated B lymphocytes that specializes in producing large amounts of a single type of antibody. It is also called plasma B cells, plasmocytes, plasmacytes, or effector B cells. Plasma cells originate in bone marrow and become differentiated into antibody producing cells upon activation by an antigen and T helper cells. Mature plasma cells are selected for producing high affinity antibodies through a process called affinity maturation. Plasma cells as used herein also encompass B cells that are induced by in vitro immunization (e.g. using conditions mimic in vivo immunization) to become antibody-producing cells.

High affinity antibodies for specific antigens are important tools for life science research and represent an important class of therapeutic molecules for treating human diseases. Many technologies have been developed to screen for high affinity monoclonal antigen-specific antibodies, for example, hybridoma technology, B-cell immortalization technologies, and phage/yeast display antibody library screen, which are usually labor intensive, time consuming and expensive to operate. Advances in single cell cloning technologies provide a new venue for making monoclonal antibodies by cloning antibody genes from single antibody producing cells, for example, memory B cells and plasma cells. Antibody gene cloning from these antibody-producing cells exploits the natural process of affinity, specificity and stability maturation, greatly reduces the downstream screening workload and increases the efficiency of finding desired antibodies. These technologies allow cloned antibodies to preserve the natural heavy and light chain cognate pairing that are selected during antibody maturation process and are more likely to find antibodies with high affinity and specificity.

Terminally differentiated plasma cells represent an excellent source for screening of high quality antibodies because they are specialized antibody-producing cells responsible for producing the majority of mature antibodies. Plasma cells also benefit from increased IgG mRNA levels compared with memory B cells, thus facilitating the recovery of antibody genes from single isolated cells. Flow cytometry is a standard method for selecting a cell subset based on surface markers. However, this technology cannot be extensively applied to select plasma cell subset due to some technical difficulties. Plasma cells have lost most surface markers during development, making it difficult to find universally acceptable plasma cell surface markers. Known human plasma cell surface markers such as CD138 (syndecan-1) and CD38 are variably expressed on plasma cells, and they are also expressed on cells other than plasma cells. In addition, the plasma cells have relatively high inherent autofluorescence. All these factors make it challenging to set appropriate gating parameters for plasma cell selection using the flow cytometry. For some species, for example, rabbits, rats, chicken, llama, goats and sheep, no surface markers specific for plasma cells have been reported. The selection methods based on surface markers are not applicable to these animal species. The present invention provides a universal method for identifying individual plasma cells independent on the availability of specific surface markers of plasma cells, which can be applied to various animal species from mammals to birds.

Instead of depending on the availability of plasma cell specific surface markers, the present invention uses high levels of intracellular IgG mRNA expression as a criterion for identifying individual plasma cells. Since mature plasma cells are specialized in generating antigen specific IgG antibodies, they generally express much more IgG mRNA than those of other types of B cells. It has been reported that plasma cells express at least 8 to 100 fold, or even up to 1000 fold more IgG antibodies than other B cell types (Hans-Martin Jack and Matthias Wabi. The EMBO Journal (1988) vol. 7(4):1041), which is a salient feature to separate plasma cells from non-plasma cells. The present invention provides a immunoglobulin mRNA-based screening method for identifying single plasma cells and cloning antibody genes from identified single plasma cells. Firstly, plasma cells are enriched from peripheral blood cells or lymphoid cells of an immunized animal using conventional surface marker based methods. Secondly, the enriched cells are dispersed into single cells in individual containers, where mRNA of individual cells are extracted and converted to cDNA, and levels of IgG mRNA are quantitatively determined for individual cells. The single cells with higher level of IgG mRNA are identified as plasma cells. Thirdly, once single plasma cells are identified, they can be used for cloning of antibody genes with native heavy chain and light chain pairs. The antibody genes can then be introduced into a cell line to express antibody proteins that can be screened for high affinity antibodies specific for the target antigen.

Collection of Source Cells Containing Plasma Cells

Plasma cells are usually isolated from organs or tissues that contain sufficient amounts of lymphocytes from an immunized animal, including, but not limited to, bone marrow, lymph nodes, spleen, tonsil, lymph, and blood. The animal may be a nonhuman animal such as rabbits, goats, chickens, llama, mice and rats that are immunized with the target antigen. Blood cells, lymphocytes or bone marrow cells collected from the vaccinated healthy human or patients infected with pathogen or recovered from pathogen infection, or patients with autoimmune disease or other diseases that generate antibodies against pathogens or pathogenic tissues can provide the source cells for isolation of human plasma cells. The methods to immunize an animal with the target antigen are well known to those with ordinary skill in the art. For example, the antigen can be administrated or inoculated into a nonhuman animal by inhalation, oral administration, subcutaneous injection, intravenous injection, intradermal injection or intramuscular injection. The nonhuman animal is immunized with the target antigen until the immunity is established. The establishment of immunity can be easily determined by collecting blood samples from the immunized animal and measuring the amount of antibodies specific for the target antigen using methods like ELISA. The frequency, duration, and quantity of antigen used can be optimized by measuring the level of antigen specific antibodies in the blood sample. Repeated exposure to the same antigen increases the proportion of plasma cells producing high affinity antibodies through a process called affinity maturation. Multiple immunization of the target antigen is thus important for generating larger immune responses and plasma cells that secrete high affinity antibodies. Once immunity to the target antigen has been established, lymphocytes cells from lymph, lymphoid tissues, blood, and bone marrow of the immunized animal can be collected as source cells for isolating plasma cells. Methods to collect lymphocytes from lymph, blood, bone marrow, spleen, lymph nodes and other lymphoid tissues are well known to those with ordinary skill in the art related to antibody technologies. For example, peripheral blood mononuclear cells (PBMCs) consisting mainly of lymphocytes and monocytes can be extracted from whole blood using ficoll and density gradient centrifugation.

Plasma cells or similar antibody producing cells may also be isolated from blood cells, lymphocytes or bone marrow derived cells sensitized by target antigen in vitro. The methods to sensitize lymphocytes to become plasma cells or similar antibody producing cells in vitro are known to those skilled in the art and are described in the published literatures, for example, US patent application No. US20140031528; Arpin C J, et al. Science (1995) 268: 720-722; Jourdan M A, et al. Blood (2009) 114: 5173-5181; Ettinger R, et al. J. Immunol. (2005) 175: 7867-7879; Minges Wols H A, et al. J. Immunol. (2002) 169: 4213-4221; Jego G, et al. Immunity (2003) 19: 225-234; Huggins J, et al. Blood (2007) 109: 1611-1619; and Geffroy-Luseau A, et al. Int. Immunol. (2008) 20: 775-782. These methods are especially useful for generating antigen specific human plasma cells that are more difficult to obtain. Briefly, PBMCs or lymphocytes collected from an unimmunized human are subject to the target antigen, antigen presenting cells (e.g. dentritic cells or helper T cells), and a cocktail of cytokines including, for example, interleukin-2 (IL-2), IL-4, IL-5, IL-6, IL-10, IL-21, interferon α (INF-α) and/or INF-γ. When cultured under appropriate conditions, B cells can be induced to differentiate into antibody producing cells similar to plasma cells, which can be used as source cells for isolating antibody producing cells that can be used for cloning of antibody genes.

Preliminary Enrichment of Plasma Cells from Source Cells

Plasma cells only account for a very small portion of source cells collected from blood or lymphoid samples, for example, <0.5% of bone marrow cells and about 0.1% of white blood cells. In order to separate single plasma cells for cloning antibody genes, different methods can be first used to enrich plasma cells from the source cells to obtain an enriched population. These methods exploit different features of plasma cells to enrich mature plasma cells on one hand and exclude undesired cells (e.g. B cells with high levels of surface IgG or surface IgM) on the other hand. For example, some known surface markers expressed on human plasma cells such as CD138, CD78, CD27 and CD319 can be used for enriching human plasma cells. Muller-Hermelink et al. (US patent publication No. 2003/0180799) reported isolation of an antibody that specifically recognizes human plasma cells, which can be used to enrich human plasma cells. These methods depend on the availability of specific surface markers or specific antibodies of the plasma cells, which may not be available for plasma cells of all species. A more general method exploits the fact that plasma cells have more abundant endoplasmic reticulum than other cell types. Using a fluorescent dye preferably staining endoplasmic reticulum than other organelles, plasma cells can be distinguished based on the higher fluorescent intensity to ER specific dyes (Kurosawa et al. US patent publication No. 2014/0013528). The efficiency of this method depends on the difference of ER-labeling fluorescence intensity between plasma cells and non-plasma cells. The bigger the difference of the fluorescence intensity, the more efficient to use this method for separating plasma cells from other cell types.

Plasma cells secret large amounts of antigen specific IgG antibodies. Although most of antibodies are extracellularly secreted from plasma cells, some of these antibodies are either attached to the surface or remain on the membrane of plasma cells, which allows plasma cells to be selected based on their ability to bind to the antigen as well as antibodies specific for IgG antibodies. When using this method to enrich plasma cells, it should be noted that the amount of the surface IgG on plasma cells is moderate, not too high or too low. The anti-IgG antibodies bind to the constant region of an IgG antibody and can recognize all IgG antibodies regardless of their antigen specificity. This method does not depend on surface markers specific for plasma cells and offers a general way to enrich plasma cells from the source cells. However, the ability to bind to the antigen and anti-IgG antibody is not unique to plasma cells. Antibodies-expressing B cells can also bind to the antigen and anti-IgG antibody. Therefore, enrichment method based on association with antigen and anti-IgG antibody can increase the portion of plasma cells in a population, but cannot specifically identify individual plasma cells.

Methods to select plasma cells based on their binding partners are well known to those skilled in the art to which this invention belongs. For example, a binding partner (e.g. a plasma cell specific antibody, an antibody for surface marker, an anti-IgG antibody, or the antigen) can be conjugated to a distinguishable label such as a fluorescent probe or a magnetic bead. Plasma cells associated with the labeled binding partner can be selected by a fluorescence-based sorting device (e.g. a flow cytometry) or magnetic bead precipitation. Depending on the availability of binding partners, one or more aforementioned methods can be used to select plasma cells from the source cells to obtain a cell population enriched with plasma cells.

In a preferred embodiment, the antigen and anti-IgG antibody are labeled with different fluorescent probes, and cells associated with fluorescently labeled antigen and anti-IgG antibody are selected by a fluorescence activated cell sorting (FACS) device. FACS is a specialized flow cytometry that can sort individual cells based on fluorescent and light scatter properties of each cell. A multicolor FACS device can be designed to distinguish up to 17-18 different fluorescent labels and can select cells based on parameters of multiple fluorescent signals. By setting appropriate selection gating parameters, single cells positively labeled with antigen and anti-IgG antibody can be selected and sorted into individual wells, which can be seamlessly integrated with downstream single cell analysis. Selecting cells double labeled with antigen and anti-IgG antibody can enrich plasma cells 100 fold from the source cells. The mature plasma cells can be further enriched by selecting the medium to large size cells and excluding B cells that expresses IgM antibodies. Mature plasma cells are reported to have medium to large size in a lymphoid cell population (Minges Wols H A and Witte P L. J Immunol Methods. (2008) 329(1-2): 219-224). FACS can also be employed to select cells based on their size. For example, the intensity of light scattered at a small angel, the forward scatter (FSC), which is determined largely by the size of the cell, can be used as a measure of cell size. In addition to select double labeled cells, choosing cells with medium to high level of FSC can further increase the proportion of plasma cells in the population. On the other hand, FACS can be used to exclude B cells that express IgM antibody. The source cells can be mixed with an anti-IgM antibody that is labeled with a third fluorescent probe. The FACS gating can be set to exclude the cells associated with fluorescently labeled anti-IgM antibody from the enriched population so as to remove IgM expressing cells.

Identification of Single Plasma Cells Based on Intracellular IgG mRNA Level

The cell population enriched with plasma cells obtained above are dispersed into single cells, each in an individual container (e.g. wells of 96-well microplates). Methods that can separate the enriched cell population into single cells and distribute each single cells into individual containers may suffice. The container is preferably to be of small size appropriate for handling materials of single cell level. For example, the cells can be dissociated into single cells and serially diluted into wells of a 96-well plate with an average of one cell per well. In a preferred example, a FACS device is used to directly sort selected single cells into individual containers. For example, the source cells can be dispersed into single cells using a conventional method and the dispersed cells are allowed to associate with antigen, anti-IgG antibody and anti-IgM antibody, each labeled with a different fluorescent probe. Single cells labeled with antigen and anti-IgG antibody, but without anti-IgM antibody, are selected and sorted to individual wells of a 96-well PCR microplate, which are directly used for downstream single-cell RNA extraction, cDNA synthesis and qPCR analysis.

After preliminary enrichment, the proportion of plasma cells in the enriched population is greatly increased compared to that of the original source cells. For example, selecting cells with double labeling of antigen and anti-IgG antibody, plasma cells can be enriched more than 100 folds. The next step is to identify single plasma cells within the enriched cell population based on quantitative determination of the intracellular level of IgG mRNA. Any method that allows quantitative determination of mRNA at single cell level and subsequent gene cloning can be used for this purpose. Generally, the method includes cell lysis, reverse transcription to generate cDNA, PCR amplification of cDNA, and quantitative determination. The quantitative determination can be performed at RNA or cDNA level, before or after amplification, as long as the detection method is sensitive enough to accurately measure the RNA or DNA levels. The preferred method is to use real time quantitative PCR (qPCR) to measure the level of IgG cDNA, which offers great sensitivity at single-cell level. Other detection methods that offer single-cell level sensitivity may be adapted to use for this purpose. For example, Porichis et al. (Nat Commun. (2016) 5: 5641. doi:10.1038/ncomms6641) describes a method to use branched DNA technology to measure mRNA at single-cell level. Briley et al. (Proc Natl Acad Sci USA. (2015) 112(31): 9591-9595) describes a method to use a spherical nucleic acid gold nanoparticle to measure specific mRNA in live cells.

When handling of RNA of single cells, extreme care needs to be executed to prevent cross-contamination, RNA degradation and material loss. Standard methods for extracting RNA from small samples include lysis of cells, binding of RNA to a mini-column, and elution of RNA in a small volume. Commercial kits for extracting RNA from small samples including single cells are available from companies such as Thermo Fisher Scientific (PicoPure® RNA Isolation Kit), Norgen Biotek (Single Cell RNA Purification Kit), and Qiagen (RNeasy micro kit). However, when handling materials of single cells, column based RNA extraction method can usually lead to significant material loss during multiple steps to remove contaminants and may not be suitable for single cell analysis. Alternatively, single cells can be lysed in a solution compatible with downstream reverse transcription and the cell lysate can be directly used, without RNA extraction, in the subsequent reverse transcription to generate cDNA. Lysis solutions compatible with reverse transcription buffer are known to people skilled in the art of molecular biology and are described in scientific literatures such as Svec et al. (Frontiers in Oncology. (2013) 3: 1-11). The lysis solutions includes, for example, 1 mg/ml BSA (bovine serum albumin), pure water, 1M trehalose, 2 mg/ml BSA and 100 µM 7-deaz GTP. Thermo Fishier Scientific (Waltham, Mass.) offers a direct lysis buffer for single cell lysis (Single cell lysis kit, catalog#4458235) containing DNase and a stop solution to inactivate DNase. The RNA released from single lysed cells can be used in a reverse transcription reaction to synthesize cDNA using methods known to people skilled in the art. The cDNA will be used as the template in the subsequent PCR for quantification of IgG mRNA level and cloning of antibody genes.

IgG protein complex is composed of four peptide chains—two identical heavy chains and two identical light chains. Both the heavy chain and the light chain have a variable region and a constant region. The constant regions of heavy or light chain contain the same sequences for each subtype of the IgG antibodies of the same animal species. The heavy chain variable region (VH) and the light chain variable region (VL) of IgGs are responsible for binding to antigens and contain different sequences that is usually optimized for binding to its antigen. To quantitate IgG mRNA level in the cell, primer pairs are designed to amplify a target sequence with 60 to 300 bp in length within the constant region of the light chain or the heavy chain. Since the nucleotide sequence of constant region is identical for each of the subtypes of IgGs, primers to amplify a target sequence within the constant region allows measuring the level of IgG mRNA. For animals with only one type of IgG (e.g. rabbit), only one pair of primers targeted to the constant region of IgG is sufficient. For animals with multiple subtypes of IgG (e.g. mouse), multiple primer pairs may need to be used with one primer pair targeted to the constant region of each subtype of the IgG. Preferably, the target sequence is within the constant region of the IgG heavy chain with a size of 80-100, 90-110, 100-150, 150-200, or 200-300 bp. A pre-amplification PCR with 8 to 20 thermal cycles are usually performed before the quantitative measurement with real time qPCR. Real time qPCR, which uses a fluorescent reporter to monitor the accumulation of DNA products during amplification cycles of PCR, is a sensitive method to measure target nucleic acid in a sample. The fluorescent reporter can be a non-specific reporter that emits fluorescent signals upon insertion into a double stranded DNA, or a sequence specific reporter that emits fluorescent signal only when binding to the complimentary sequence on the target DNA. The number of cycles at which fluorescence exceed the threshold level is called the threshold cycle (Ct) or quantification cycle (Cq). Ct is used to quantify the amount of original nucleic acids in the sample, where higher Ct indicates a lower amount of original materials. Depending on the amplification efficiency, one cycle difference between two samples indicates about 2 fold difference of original materials in the two samples. As specialized antibody-producing cells, plasma cells express much more immunoglobulins, mostly IgGs, than non-plasma cells. This is a unique feature that separates plasma cells from other cell types. It is reported that plasma cells can express 8-100 fold or up to 1000 fold more IgGs than non-plasma cell. This is approximately 3 to 6 or up to 10 cycle difference in Ct. For the sorted cells, they can be divided into three distinguishable groups based on their IgG expression level: a group with high expression of IgG (e.g. a Ct of 21-24), a group with low expression of IgG (e.g. a Ct of 30-32), and a group with very low/no expression of IgG (e.g. no signal after 40 PCR cycles). The group with high expression of IgG is identified as plasma cells. The group with low expression of IgG is likely to contain other B cells than plasma cells. The group with very low/no expression of IgG may contain non-B cells or even no cells at all. Because plasma cells express significantly more IgG than non-plasma cells, plasma cells can be easily identified based on the intracellular IgG mRNA level.

In one embodiment of the present invention, the quantitative measurement of the IgG expression level is performed simultaneously with PCR amplification to clone antibody genes wherein a fluorescent dye is added in the PCR system to monitor the formation of PCR products. In this scenario, no separate quantitative PCR is performed. The qPCR quantification allows identification of the group of cells with high levels of expression of IgG, which are identified as plasma cells. The subsequent amplification, cloning, expression and screening are performed only in the identified plasma cells, resulting in significant saving in time and materials.

Cloning Antibody Genes from Single Plasma Cells

Once single plasma cells are identified, IgG genes can be amplified from cDNA of the identified plasma cells using multiple rounds of PCRs. The cloning of IgG genes can be performed to obtain the full length heavy and light chain, or only the variable regions. The variable regions of the heavy and light chains can then be linked to the respective constant regions of heavy and light chains to assemble the full length the heavy and light chain, respectively. Or the variable regions can be connected with constant regions to make antigen-binding fragments (Fab). The heavy and light chains are assembled independently and co-expressed in host cells to make functional antibodies or antibody fragments that can bind to antigens. The methods to clone the heavy and light chains of IgG from single cells are known to people skilled in the art and can be found in the public literatures such as Coronella et al. (Nucleic Acids Research. 2000, 28(20): e85) and Clargo et al. (MAbs. 2014, 6(1):143-59).

In the first PCR to amplify variable regions, primer pairs are designed to separately amply the variable region of heavy or light chain of IgG antibody. IgG antibodies of some animal species have different subtypes of heavy chains and multiple light chains, which may require a primer pair for each subtype of heavy or light chain. For example, human IgG has four subtypes of heavy chains and two different types of light chains. Four pairs of heavy chain primers and two pairs of light chain primers may be needed to cover all the human IgG antibody subtypes. The 3' and 5' primers are designed to anneal to the constant region and the 5' conserved region of the "leader sequence" or "frame region", respectively. The constant region of the heavy and light chain is quite conserved for each subtype of IgGs of the same animal species. A 3' primer can be designed in the conserved region of the constant region using a conventional primer design program. Designing 5' primers can be more challenging because of the diversity of the variable region of IgG antibodies. The 5' primer are usually designed in the "Leader peptide" or "Framework" region at the 5' end of the variable region, which tends to have more conserved sequences. The design of 5' primer is usually based on the most conserved region in the leader peptide or framework region. The 5' primer may be designed as a universal primer based on the consensus sequence of the conserved region, in which degenerate nucleotide may be used. Or the 5' primer may be made of a set of primers, each being best matched to a IgG subtype sequences. Ideally, the universal primer or the primer set is able to cover all the antibody genes and effectively amplify the variable region genes in single plasma cells. Another method for amplifying variable regions of IgG gene from the plasma cell cDNA is to add a polynucleotide tail, usually a polyG or polyC tail, to the 3' end of cDNAs during the reverse transcription reaction. The 5' primer can then use a polynucleotide sequence that is complementary to the polynucleotide tail on the cDNAs (Zhu Y Y, et al. *BioTechniques*. (2001) 30:892-897).

Once the variable region is amplified from the IgG cDNA via the first PCR, a second nested PCR is used to further amplify the cloned variable regions. The second PCR can also be used to add elements (e.g. overlapping insertion sequence) to the variable region so that it can be connected to the constant region in an expression vector or expression cassette containing appropriate regulatory components for transcription (e.g. a promoter and a poly-adenylation sequence). This will result in two separate transcriptionally active products, one encoding a heavy chain and the other a light chain. The transcriptionally active product can be a linear DNA or an expression vector containing the transcription regulatory elements and a heavy or light chain with both the variable and constant regions. The variable region can be assembled with the constant region of the same animal species, or it can be recombined with the constant region of a different animal species to produce a chimeric antibody. For example, rabbit variable regions can be assembled with human constant regions to make a humanized antibody. Because the sequences of cloned variable regions are unknown, it is hard to choose a restriction enzyme for inserting the cloned genes into the expression vector. A preferred method for inserting cloned variable regions into an expression vector or cassette is seamless cloning, such as Gibson Assembly method (Gibson D G, et al. Nat Methods. (2009) 6(5):343-5), which allows assembly of DNA fragments with overlapping ends without using restriction enzymes. In the second PCR, insertion sequences of 12-30 nt can be added to the ends of 5' and 3' primers, which overlap with the sequences at insert site of the expression vector. Alternatively, the overlapping sequence can be added into the expression vector so that the cloned genes and the expression vector with the same overlapping end sequence can be linked together using Gibson Assembly method. The Gibson method uses an exonuclease to digest the 5' end of dsDNA fragments, leaving a 3' overhang. The DNA fragments with complementary 3' overhangs anneal together, any gap is filled by DNA polymerase and adjacent segments are ligated together by DNA ligase, resulting the cloned variable gene seamlessly connected to the constant region in the expression vector.

Expressing Antibody Genes and Screening for High Affinity Antibodies Specific for the Antigen The native pair of transcriptionally active heavy and light chain from the same plasma cells can be introduced into appropriate host cells to express the fully functional antibody specific for the antigen. The cells used for expression of the antibody can be any host cells suitable for expression of foreign proteins, including yeasts, phage, bacteria (e.g. *E. coli* cells), insect cells (e.g. sf-9 and sf-21 cells) and mammalian cells (e.g. HEK293 and CHO cells). Despite the high production cost and difficulty in handling, mammalian cells are still the preferred choice for expression of recombinant antibodies because they allow complex folding patterns, post-translational modification, and secretory expression. The antigen binding activity of recombinant antibody can be assessed by conventional immunoassays like ELISA, which is well known to people skilled in the art. For example, the sandwich ELISA is commonly used for this purpose. The solution with recombinant antibodies is incubated in an antigen coated microplate. After removing the unbound free antibodies, the antibodies bound to the immobilized antigen can be visualized by a HRP conjugated secondary antibody that recognizes the bound antibodies.

EXAMPLES

The following examples are provided by way of illustration only, not by way of limitation. It is not intended to use these examples to limit the scope of the invention, which is only defined by the appended claims. The following example illustrates the method to clone rabbit antibody genes encoding antibodies specific for human Lipoprotein-associated phospholipase A2 (LP-PLA2) from single plasma cells.

Example 1. Antigen Preparation and Animal Immunization

Antigen (Human LP-PLA2) Preparation

C-terminal His-tagged full-length human LP-PLA2 gene was synthesized with *E. coli* codon optimization, cloned into bacterial expression vector pET28a (EMD Millipore, San Diego, Calif.) and transformed into *E. coli* strain BL21 (DE3). Colonies were inoculated in terrific broth and cultured at 37° C., 250 rpm. After $OD_{600}$ reached 2.5, the incubator was cooled down to 18° C. and 1 mM IPTG was added for inductive expression of LP-PLA2 protein. After overnight expression, *E. coli* were harvested and pellets were extracted with a binding buffer (50 mM $NaH_2PO_4$, 300 mM NaCl, 10 mM Imidazole, pH8.0). After loaded on nickel column followed by extensive wash (wash buffer, 50 mM $NaH_2PO_4$, 300 mM NaCl, 20 mM imidazole, pH 8.0), LP-PLA2 protein was eluted with an elute buffer (50 mM $NaH_2PO_4$, 300 mM NaCl, 250 mM imidazole). LP-PLA2 protein was further buffer exchanged by dialyzing against PBS (50 mM potassium phosphate, pH7.2; 150 mM NaCl) overnight. The purified protein had a purity >95% when tested on an SDS-PAGE gel. The purified LP-PLA2 protein was aliquoted and frozen for immunization and screening.

Immunization

Three white New Zealand rabbits were immunized as the following schedule.

week 0: immunize 200 μg/rabbit in Complete Freund's Adjuvant (CFA) solution
week 3: immunize 100 μg/rabbit in Incomplete Freund's Adjuvant (IFA) solution
week 5: immunize 100 μg/rabbit in IFA
week 7: immunize 100 μg/rabbit in IFA
week 8: bleed 3 ml blood
week 9: immunize 100 μg/rabbit in IFA
week 10: Sacrifice rabbit #1, take bone marrow
week 12: Immunize 100 μg/rabbit in IFA
week 13: Sacrifice rabbit #2, take bone marrow
week 14: Immunize 100 μg/rabbit in IFA
week 15: Sacrifice rabbit #3, take lymph nodes and bone marrow.

Example 2. Plasma Cell Enrichment Using FACS

Bone Marrow and Lymph Nodes Cell Preparation

Bone marrow or lymph nodes from the above immunized rabbits were rinsed in cold RPMI1640 medium (Thermo Fishier Scientific, Waltham, Mass.) and minced. After macerated through a 70 μm cell strainer, centrifuge the minced tissue at 450 g for 2 minutes. The cell pellet was resuspended in cold RPMI1640 with 2% FBS. Layer 6 ml of the cell suspension onto a 3 ml of Ficoll-Hypque gradient (density=1.084, GE) and centrifuge at 3000 g for 30 minutes at 4° C. Cells at the interphase were collected and washed twice with PBS containing 2% FBS.

After filtering the cells with a cell strainer, incubate the cells with 0.1 μg/ml Dylight 650 conjugated anti-rabbit IgG (catolog# ab97077 Abcam, Cambridge, UK) and Dylight 488 conjugated antigen, LP-PLA2 (final concentration 0.5 μg/ml) on ice for 30 min in the dark. Subsequently, cells were washed 2 times with PBS containing 2% FBS. Cells were ready to sort.

Plasma Cell Enrichment by FACS

The cells were sorted using an FACS sorter that allows dispensing single cells with desired characteristics into individual wells of a 96-well PCR plate. The cells were gated for positive anti-IgG and high PLA2 labeling. The cells with strong labeling of PLA2 (Dylight 488 labeling) and moderate labeling of anti-IgG antibody (Dylight 650 labeling) were individually deposited in wells of a 96-well PCR plate with one cell per well. The cells were lysed in a lysis buffer (single cell lysis kit, catlog#4458235, Thermo Fishier Scientific, Waltham, Mass.) and spun down for 2 minutes at 400 g. The cell lysate was frozen and stored at −80° C.

Example 3. qPCR Screening for Single Plasma Cells

The IgG mRNA of each selected cell was determined using quantitative PCR techniques to identify plasma cells which have high levels of IgG expression.

Firstly, mRNA of each selected cell was extracted and reverse transcribed into cDNA following the vendor protocol (Superscript IV First-strand Synthesis System, catolog#18091200, Thermo Fishier Scientific, Waltham, Mass.). Briefly, the frozen cell lysate was thawed from the plates and 15 μl of the mixture of reverse transcription reagents was added to each well. After heating on a thermocycler at 60° C. for 5 min, incubate the mixture at 55° C. for 10 min, and inactivate the reaction by incubating it at 80° C. for 10 min.

The mixture of reverse transcription reagents was prepared as follows:
Add DEPC-treated water to 15 μL
5×SS-IV Buffer 4.0 μL
reverse transcriptase 1.0 μL
10 mM dNTP mix (10 mM each) 1.0 μL
100 mM DTT 1.0 μL
Ribonuclease Inhibitor (40 U/μL) 1.0 μL
50 μM Oligo d(T)$_{20}$ primer, or
50 ng/μ L random hexamers 1.0 μL Secondly, a two-step PCR analysis was performed to quantitate the IgG RNA transcripts in each of the single cells, which included a pre-amplification PCR with 14 thermal cycles and a real-time quantitative PCR (qPCR) with 40 thermal cycles. The PCR primers were designed to amplify a 95 bp nucleotide sequence within the constant region of heavy chain of rabbit IgG. For the pre-amplification PCR, the forward and backward primer is caccaaagtggacaagac (SEQ ID NO:1) and ggaagatgaagacagacg (SEQ ID NO:2). The same primer pair was used for quantitative PCR, and a sequence specific fluorescent reporter ([6FAM]TTGCACCCTCGACATGCAGC[BHQ1], SEQ ID NO:3) was added to monitor the production of the target DNA product as the PCR reaction progresses.

The qPCR assay showed that the sorted cells can be divided into three distinguishable groups based on their IgG expression level: a group of cells having high expression of IgG, a group of cells having low expression of IgG and a group of cells having very low/no expression of IgG. The group with high levels of IgG expression usually have 8 to 1000 fold more IgG mRNA than that of the group with low IgG, which can be clearly distinguishable by analyzing the qPCR data. The group with high expression of IgG is identified as plasma cells. The group with low expression of IgG is likely to contain B cells other than plasma cells. The group with very low/no expression of IgG may contain non-B cells or even no cells at all.

Conditions for performing the PCR is as follows:
Pre-Amplification PCR Using NEB Taq Polymerase (NEB, Cat# M0273)
Primer Pair:
RabHCVis-F caccaaagtggacaagac (SEQ ID NO:1)
RabHCVis-R ggaagatgaagacagacg (SEQ ID NO:2)
Product size: 95 nt
Template: cDNA preparation made above Reaction Setup:
Component 25 µl Reaction Final Concentration
10× Standard Taq Reaction Buffer 2.5 µl 1×
10 mM dNTPs 0.5 µl 200 µM
10 µM Forward Primer 0.5 µl 0.05 µM
10 µM Reverse Primer 0.5 µl 0.05 µM
Template DNA 1 µl
Taq DNA Polymerase 0.125 µl
Nuclease-free water to 25 µl
Pre-Amplification PCR Conditions:
95° C.×30"
95° C.×15"
60° C.×4'×14 cycles
99° C.×10' to inactivate Taq DNA Polymerase
Real Time PCR Using TaqMan® Real-Time PCR Master Mix
on Bio-Rad CFX real-time Thermocycler.
Template: pre-amplified PCR products
Primer:
   RabHCVis-F caccaaagtggacaagac (SEQ ID NO:1)
   RabHCVis-R ggaagatgaagacagacg (SEQ ID NO:2)
Fluorescent Probe:
   RabVisual Probe Sequence:
   [6FAM]TTGCACCCTCGACATGCAGC [BHQ1] (SEQ ID NO:3)
Reaction Setup
   TagMan Fast Universal PCR master (2×) 10 µl
   Primer (RabHCVis-F) 900 nM
   Primer (RabHCVis-R) 900 nM
   Probe (RabVisual) 250 nM
   Pre-amplified product(cDNA) 5 µl
   Water to 20 µl
PCR Condition:
   95° C.×10'
   95° C.×5"
   60° C.×1'×40 cycles Example 4. Amplification of the Variable Region of Antibody Genes The cDNA of plasma cells identified from the qPCR screening was used as the template to amplify cognate pairs of variable region of heavy chain (VH) and variable region of light chain (VL) via two rounds of PCR. The first PCR used gene specific primers for both the 3' and 5' ends. The 5' primer anneals to a conserved region at 5' end of the variable region of rabbit IgG genes and the 3' primer anneals to the constant region of respective heavy or light chain. The forward and reverse primers of the first PCR for amplification of VH are RabIgHL-F1 (gcttctcctggtcgctgtg, SEQ ID NO: 4) and RabIgHC-R (tcttgtccactttggtgttgg, SEQ ID NO:5), respectively. The forward and reverse primers of the first PCR for amplification of VL are RabIgKL-F1 (gggctctgctgctctgg, SEQ ID NO:6) and RabIgKL-R1 (atggtgggaagaKgaggaca, SEQ ID NO:7), respectively. The PCR reactions were performed with Phusion DNA polymerase kit (New England Biolabs, Ipswich, Mass.). The second PCR was performed to further amplify the VH and VL genes. The forward and reverse primers for the second PCR for amplification of VH is RabIgHC-NestedF cttctcctggtcgctgtgctc (SEQ ID NO:8) and RabIgHC-nestedR accgtggagctgggtgtgt (SEQ ID NO:9), respectively. The forward and reverse primers for the second PCR for amplification of VL is RabIgKL-nestedF2 tgctctggctcccaggtg (SEQ ID NO: 10) and RabIgKC-NestedR3 atggtgggaagaKgaggacagtagg (SEQ ID NO:11), respectively.

The mammalian expression vectors pRab293H2 containing the constant region of the heavy chain and pRab293L3 containing the constant region of the light chain (Backliwal G et al. Nucleic Acids Res. 2008 September; 36(15):e96.) are used to assembly functional antibody genes with variable and constant regions of the heavy and light chain of rabbit IgG, respectively. The expression vectors are constructed with 5' leader region and 3' constant region that overlap with the 5' and 3' ends of the cloned variable gene products of the second PCR. With the overlapping sequences in the cloned variable region genes and the expression vector, the variable region genes are seamlessly connected to the constant region in the expression vector using the Gibson Assembly® Master Mix (cat# E2611L, New England Biolabs, Ipswich, Mass.). Briefly, amplified variable region DNAs were mixed with linearized expression vector in Gibson assembly master mix containing exonuclease, DNA polymerase and Taq DNA ligase. The mixture were incubated at 50° C. for 15-20 minutes and it was ready for transformation.

PCR Amplification for VH
$1^{st}$ PCR
   RabIgHL-F1 gcttctcctggtcgctgtg (SEQ ID NO:4)
   RabIgHC-R tcttgtccactttggtgttgg (SEQ ID NO:5)
   Primer: 1 µM each
$1^{st}$ PCR Thermal Cycle Settings
   98° C.×15
   98° C.×6"
   68° C.→60° C.×1'×8 cycles, −1° C./cycle; 60° C.×15"×25 cycles
   72° C.×30"
$2^{nd}$ PCR
   RabIgHC-NestedF cttctcctggtcgctgtgctc (SEQ ID NO:8)
   RabIgHC-nestedR accgtggagctgggtgtgt (SEQ ID NO:9)
   Template: 1:10 dilution of the $1^{st}$ PCR products
$2^{nd}$ PCR thermal cycle setting:
   98° C.×15"
   98° C.×6"
   65° C.×15"
   72° C.×30"
   ×35 cycles
PCR amplification for VL
$1^{st}$ PCR
   RabIgKL-F1 gggctcctgctgctctgg (SEQ ID NO:6)
   RabIgKL-R1 atggtgggaagaKgaggaca (SEQ ID NO:7)
$1^{st}$ PCR Thermal Cycle Settings
   98° C.×15"
   98° C.×6"
   68° C.→60° C.×1' (−1° C./cycles, ×8 cycles)
   72° C.×30"
   60° C.×15"×25 cycles
$2^{nd}$ PCR
   RabIgKL-nestedF2 tgctctggctcccaggtg (SEQ ID NO: 10)
   RabIgKC-NestedR3 atggtgggaagaKgaggacagtagg (SEQ ID NO:11)
   Template: 1:10 dilution of the $1^{st}$ PCR product
$2^{nd}$ PCR thermal cycle setting:
   98° C.×6"
   63° C.×15"×35 cycles
   72° C.×30"

Example 5. Expressing and Screening for Antigen-Specific Antibodies

The expression vectors assembled with a functional heavy or light chain were transformed into *E. coli* DH10B competent cells (catolog#18297-010, Thermo Fisher Scientific) and spread on a LB plate (10 g tryptone, 5 g yeast extra and 10 g NaCl in 1 liter deionized water) containing carbenicillin antibiotics, and incubated at 37° C. for overnight. Two colonies for each well were inoculated to make plasmid DNA for transfection and expression in HEK293 Cells. The plasmid DNA was transfected into HEK293F cells ($1\times10^6$ cells/ml) using FreeStyle™ MAX reagent from Thermo Fishier Scientific (catalog#16447-100) on a 96-deep well plate. Transfected cells were covered with an air-permeable filter and cultured at 37° C., 8% $CO_2$, at a shaking speed of 300 rpm for 2 days. Harvest the supernatants for ELISA assay.

Sandwich ELISA was used to screen for recombinant genes encoding antigen specific antibodies. An ELISA plate was coated with 2 µg/ml of *E. coli* expressed LP-PLA2 antigen (Example 1) in PBS overnight at 4° C. After blocking with PBS containing 1% BSA, 50 µl of supernatants from transfected HEK293F were added and incubated for 1 hour at room temperature. After the plates were washed with PBS-T (PBS with 0.1% tween-20), HRP-conjugated goat anti-rabbit IgG, (GE Bioscience, catolog# RPN4301) diluted 1:2000 in PBS-T with 1% BSA was added to detect the antibodies bound to the immobilized LP-PLA2 and incubated for 30 minutes at room temperature. The plates were washed in PBS-T before addition of 100 ul of TMB substrate. 50 ul of 0.5M sulfuric acid was added after 10 min incubation to stop the reaction. Signal was detected on an ELISA plate reader at wavelength of 450 nm.

The data from screening indicates that about 20% of the sorted cells are plasma cells and 30% of these plasma cells produce antigen specific antibodies (Table 1).

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

REFERENCES

Aishun J, et al. A rapid and efficient single-cell manipulation method for screening antigen-specific antibody—secreting cells from human peripheral blood. nature medicine. (2009) 15(9): 1088-92

Arpin C, et al. Generation of memory B cells and plasma cells in vitro. Science (1995) 268: 720-722.

Backliwal G, et al. Rational vector design and multi-pathway modulation of HEK 293E cells yield recombinant antibody titers exceeding 1 g/l by transient transfection under serum-free conditions. Nucleic Acids Res. (2008) 36(15):e96.

Clargo A M, et al. The rapid generation of recombinant functional monoclonal antibodies from individual, antigen-specific bone marrow-derived plasma cells isolated using a novel fluorescence-based method. MAbs. (2014) 6(1):143-59

Corti D, et al. Efficient Methods to Isolate Human Monoclonal Antibodies from Memory B Cells and Plasma Cells. Microbiology Spectrum (2014) 2(5): 1

Ettinger R, et al. IL-21 induces differentiation of human naive and memory B cells into antibody-secreting plasma cells. J. Immunol. (2005) 175: 7867-7879.

Geffroy-Luseau A, et al. Osteoclasts support the survival of human plasma cells in vitro. Int. Immunol. (2008) 20: 775-782.

Gibson D G, et al. Enzymatic assembly of DNA molecules up to several hundred kilobases. Nat Methods. (2009) 6(5):343-5.

Hans-Martin Jack and Matthias Wabi. Immunoglobulin mRNA stability varies during B lymphocyte differentiation The EMBO Journal (1988) vol. 7(4):1041.

Huggins J, et al. CpG DNA activation and plasma-cell differentiation of CD27− naive human B cells. Blood (2007)109: 1611-1619.

Jack H M and Wabi M. Immunoglobulin mRNA stability varies during B lymphocyte differentiation. The EMBO Journal (1988) vol. 7(4):1041.

Jego G, et al. Plasmacytoid dendritic cells induce plasma cell differentiation through type I interferon and interleukin 6. Immunity (2003)19: 225-234.

Jourdan M, et al. An in vitro model of differentiation of memory B cells into plasmablasts and plasma cells including detailed phenotypic and molecular characterization. Blood. (2009)114: 5173-5181.

Kurosawa N and Isobe M. U.S. application Ser. No. 14/008, 567. Method for selecting plasma cells or plasmablasts, method for producing target antigen specific antibodies, and novel monoclonal antibodies.

Minges Wols H A and Witte P L. Plasma cell purification from murine bone marrow using a two-step isolation approach. J Immunol Methods. (2008) 329(1-2): 219-224.

Minges-Wols H A, et al. The role of bone marrow-derived stromal cells in the maintenance of plasma cell longevity. J. Immunol. (2002) 169: 4213-4221.

Sal T Reddy, et al. Monoclonal antibodies isolated without screening by analyzing the variable-gene repertoire of plasma cells. Nature Biotechnology (2010) 28:965-969

Scheid J F, et al. Broad diversity of neutralizing antibodies isolated from memory B cells in HIV-infected individuals. Nature. (2009) 458(7238): 636-40.

Seeber S, et al. A robust high throughput platform to generate functional recombinant monoclonal antibodies using rabbit B cells from peripheral blood. PLoS One. (2014) 9(2):e86184.

Zhu Y Y, et al. Reverse transcriptase template switching: A SMART™ approach for full-length cDNA library construction. *BioTechniques*. (2001) 30:892-897.

What is claimed is:

1. A method for cloning antigen-specific antibody genes from single plasma cells, comprising the steps of:
   a) collecting a population of cells enriched with plasma cells expressing antibodies specific for said antigen;
   b) dispersing said population of cells enriched with plasma cells as single cells into individual containers;
   c) measuring the amount of IgG mRNA in each of said single cells and dividing said single cells into groups with high and low levels of IgG mRNA, wherein cells in the high IgG group express significantly more IgG mRNA than those in the low IgG group, and wherein single cells with high levels of IgG mRNA are identified as plasma cells; and
   d) cloning and amplifying said antigen-specific antibody genes from said identified single plasma cells.

2. The method of claim 1, further comprising expressing said antigen-specific antibody genes and screening for antibody genes encoding antibodies specific for said antigen.

3. The method of claim 2, wherein said antigen-specific antibody genes are introduced into host cells for expressing antibody proteins and screening for antibodies with antigen binding activities.

4. The method of claim 1, wherein said population of cells enriched with plasma cells is collected from source cells of blood, lymph, bone marrow, spleen, tonsil, lymph nodes, or other lymphoid tissues from an animal immunized with said antigen or from blood cells, lymphocytes or bone marrow derived cells sensitized by said antigen in vitro.

5. The method of claim 4, wherein the method to enrich plasma cells in said population of cells is selecting cells that bind to said antigen, anti-plasma cell antibodies, anti-plasma cell specific markers antibodies, endoplasmic reticulum-specific dyes, anti-IgG antibody, or any combination thereof.

6. The method of claim 1, wherein IgG mRNA levels of said single cells in step c) are measured using quantitative PCR.

7. The method of claim 6, wherein the quantitative PCR measurement is combined with the PCR for amplifying the antigen-specific antibody genes.

8. The method of claim 1, wherein single cells with high levels of IgG mRNA have 8 to 10000 fold more IgG mRNA than those with low levels of IgG mRNA.

9. The method of claim 1, wherein single cells with high levels of IgG mRNA have 8 to 100 fold more IgG mRNA than those with low levels of IgG mRNA.

10. The method of claim 1, wherein single cells with high levels of IgG mRNA have 100 to 1000 fold more IgG mRNA than those with low levels of IgG mRNA.

11. The method of claim 1, comprising the steps of:
    a) collecting source cells from blood, lymph, bone marrow, lymph node, and/or other lymphoid tissues of an animal immunized with said antigen, or from blood cells, lymphocytes or bone marrow derived cells that are sensitized to said antigen in vitro;

b) obtaining a population of cells enriched with plasma cells by selecting cells from said source cells that bind to said antigen and anti-IgG antibody;
c) dispersing said population of cells enriched with plasma cells as single cells into individual containers;
d) measuring IgG mRNA levels in each of said single cells and dividing said single cells into groups with high and low levels of IgG expression, wherein cells in the high IgG group express significantly more IgG mRNA than those in the low IgG group, and wherein single cells with high levels of IgG expression are identified as plasma cells;
e) amplifying and cloning said antigen-specific antibody genes from said identified single plasma cells; and
f) introducing said antigen-specific antibody genes into a host cell and screening for antibody genes that encode antibodies specific for said antigen.

12. The method of claim 11, wherein the IgG mRNA level in said single cells are measured using quantitative PCR.

13. The method of claim 11, wherein the step b) comprises using fluorescence activated cell sorting method to select cells that bind to fluorescently labeled antigen and anti-IgG antibody.

14. The method of claim 11, wherein the step b) further comprises excluding IgM positive cells.

15. The method of claim 11, wherein said antigen-specific antibody genes are transfected into and expressed in HEK 293 cells.

16. The method of claim 11, wherein said source cells are from a nonhuman animal.

17. The method of claim 11, wherein said source cells are from a human.

18. The method of claim 11, wherein variable regions of the heavy and light chain of IgG are cloned from said identified single plasma cells.

* * * * *